United States Patent
Li et al.

(10) Patent No.: US 10,495,446 B2
(45) Date of Patent: Dec. 3, 2019

(54) METHODS AND APPARATUS FOR MEASURING HEIGHT ON A SEMICONDUCTOR WAFER

(71) Applicant: KLA-Tencor Corporation, Milpitas, CA (US)

(72) Inventors: Shifang Li, Pleasanton, CA (US); Guoheng Zhao, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/192,962

(22) Filed: Jun. 24, 2016

(65) Prior Publication Data

US 2016/0377412 A1  Dec. 29, 2016

Related U.S. Application Data (60) Provisional application No. 62/186,215, filed on Jun. 29, 2015.

(51) Int. Cl.
*G01B 11/06* (2006.01)
*G01N 21/956* (2006.01)
(Continued)

(52) U.S. Cl.
CPC ...... *G01B 11/0608* (2013.01); *G01B 11/0641* (2013.01); *G01N 21/9501* (2013.01);
(Continued)

(58) Field of Classification Search
CPC ............ G01B 11/0608; G01B 2210/56; G01N 21/9501; G01N 21/956; H01L 22/00
See application file for complete search history.

(56) References Cited

U.S. PATENT DOCUMENTS

| 5,442,189 A | 8/1995 | Tsuneyuki |
| 5,581,345 A * | 12/1996 | Oki ................... G01B 11/0608 356/4.01 |

(Continued)

FOREIGN PATENT DOCUMENTS

| CN | 101231158 A | 7/2008 |
| CN | 203337093 U | 12/2013 |

(Continued)

OTHER PUBLICATIONS

English translation of foreign patent document JP 2001-124530.*

(Continued)

*Primary Examiner* — Michael A Lyons
(74) *Attorney, Agent, or Firm* — Kwan & Olynick LLP (57) ABSTRACT

Disclosed are apparatus and methods for determining height of a semiconductor structure. The system includes an illumination module for directing one or more source lines or points towards a specimen having multiple surfaces at different relative heights and a collection module for detecting light reflected from the surfaces. The collection module contains at least two detectors with one slit or pinhole in front of each detector that that are positioned to receive light reflected from one of the surfaces. A first detector receives reflected light from a slit or pinhole that is positioned before a focal point, and a second detector receive reflected light from a slit or pinhole that is positioned after the focal point so that the first and second detector receive light having different intensity values unless the surface is at an optimum focus. The system includes a processor system for determining a height based on the detected light received by the detectors from two of the surfaces.

17 Claims, 8 Drawing Sheets

(51) Int. Cl.
*H01L 21/66* (2006.01)
*G01N 21/95* (2006.01)

(52) U.S. Cl.
CPC ........... *G01N 21/956* (2013.01); *H01L 22/12* (2013.01); *G01B 2210/56* (2013.01)

(56) References Cited

U.S. PATENT DOCUMENTS

| | | |
|---|---|---|
| 6,603,541 B2 | 8/2003 | Lange |
| 6,646,281 B1 | 11/2003 | Krantz et al. |
| 6,657,216 B1 | 12/2003 | Poris |
| 6,693,664 B2 | 2/2004 | Neumann |
| 6,858,859 B2 | 2/2005 | Kusunose |
| 6,872,942 B1 | 3/2005 | Adler |
| 7,106,432 B1 | 9/2006 | Mapoles et al. |
| 7,477,401 B2 | 1/2009 | Marx et al. |
| 7,486,392 B2 | 2/2009 | Yang et al. |
| 7,961,763 B2 | 6/2011 | Furman et al. |
| 8,319,978 B2 | 11/2012 | Ben-Levi et al. |
| 8,854,613 B2 | 10/2014 | Fujihara |
| 9,021,406 B2 | 4/2015 | Hashimoto |
| 9,885,656 B2 | 2/2018 | Li et al. |
| 2012/0026511 A1 | 2/2012 | Ohkubo et al. |
| 2014/0152797 A1* | 6/2014 | Mitsuhiro .......... G01N 21/8806 348/79 |
| 2015/0106057 A1* | 4/2015 | Sugita ................ G01B 11/0608 702/167 |
| 2015/0168311 A1 | 6/2015 | Seki et al. |

FOREIGN PATENT DOCUMENTS

| | | |
|---|---|---|
| EP | 0294643 B1 | 3/1994 |
| JP | 09325278 A | 12/1997 |
| JP | 2001124530 A | 5/2001 |
| JP | 2001311608 A | 11/2001 |
| JP | 2006030039 A | 2/2006 |
| JP | 2010112803 A | 5/2010 |
| JP | 2012068201 A | 4/2012 |
| WO | 2014164935 A | 10/2014 |

OTHER PUBLICATIONS

English translation of foreign patent document JP 2001-311608.*
"International Application Serial No. PCT/US2016/039900, Search Report dated Nov. 2, 2016", 4 pgs.
European Search Report Application No. 16818625.2, dated Jun. 12, 2018, 7 Pages.
Application No. 201680032048.8, filing date Jun. 28, 2016, Chinese Office Action dated Sep. 4, 2019, English Translation, 8 pages.

* cited by examiner

METHODS AND APPARATUS FOR MEASURING HEIGHT ON A SEMICONDUCTOR WAFER

CROSS-REFERENCE TO RELATED APPLICATIONS

This application claims the benefit of prior application U.S. Provisional Application No. 62/186,215, filed 29 Jun. 2015 by Shifang Li et al., which application is herein incorporated by reference in its entirety for all purposes.

TECHNICAL FIELD OF THE INVENTION

The present invention relates generally to methods and systems for characterization of semiconductor wafers and, more specifically, to determine the height of structures or surfaces on a semiconductor wafer.

BACKGROUND

Photolithography or optical lithography systems used in the manufacture of integrated circuits have been around for some time. Such systems have proven extremely effective in the precise manufacturing and formation of very small details in the product. In some photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with a material sensitive to irradiation, e.g., photoresist. The exposed photoresist typically forms a pattern that after development masks the layers of the wafer during subsequent processing steps, as for example deposition and/or etching.

Due to the large scale of circuit integration and the decreasing size of semiconductor devices, the reticles and fabricated devices have become increasingly sensitive to feature variations, such as critical dimension (CD), height, film thickness and composition, etc. In a specific example, three dimensional (3D) inspection and metrology are often used in the semiconductor industry, such as for evaluating TSV (through silicon via) and bump structures, or particle shape (size and height). Height variations, if uncorrected, can cause the final device to fail to meet the desired performance due to electrical timing errors. Even worse, they can cause the final device to malfunction and adversely affect yield.

In view of the foregoing, improved metrology apparatus and techniques for determining structure height are needed.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a system for determining height of a semiconductor structure is disclosed. The system includes an illumination module for directing one or more source lines or points towards a specimen having a plurality of surfaces at different relative heights and a collection module for detecting light reflected from the surfaces. The collection module contains at least two detectors that are positioned to receive light reflected from a one of the surfaces. A first one of the detectors receives more reflected light from a position before a focal point and a second one of the detectors receives more reflected light from a position after the focal point so that the first and second detector receive light having different intensity values unless such one of the surfaces is at an optimum focus. The system also includes a processor system for determining a height based on the detected light received by the at least two detectors from two of the surfaces.

In a specific implementation, the illumination module comprises a pinhole for receiving illumination light and directing a source point of the illumination onto the specimen and the collection module further comprises (i) a first pinhole positioned before the focal point through which a portion of the reflected light is passed to the first detector and (ii) a second pinhole positioned after the focal point through which a portion of the reflected light is passed to the second detector. The first and second detectors are photodiode detectors.

In another embodiment, the illumination module comprises a slit for receiving illumination light and directing a source line of the illumination onto the specimen. The collection module further comprises (i) a first slit positioned before the focal point through which a portion of the reflected light is passed to the first detector and (ii) a second slit positioned after the focal point through which a portion of the reflected light is passed to the second detector. The first and second detectors are photodiode arrays.

In one aspect, the collection module further comprises a pair of pinholes or slits that are positioned such that the focal point reflected from an in-focused or de-focused surface is received between or on one of such pinholes or slits. In a further aspect, the pair of pinholes or slits are positioned so as to receive different amounts of light when one of the surfaces is de-focused and equal amounts of light when such surface is in focus. In yet another aspect, the pair of pinholes or slits are positioned so that only one of the first and second detectors receive a maximum intensity from a particular one of the surfaces when it is de-focused by a particular amount.

In another embodiment, the illumination module comprises a slit for receiving illumination light and directing a source line of the illumination onto the specimen. In this embodiment, the first detector is positioned before the focal point, and the second detector is positioned after the focal point. In yet another aspect, the illumination module comprises a plurality of slits or pinholes for receiving illumination light and directing a plurality of source lines or points of the illumination onto the specimen, and the at least two detectors are two dimensional image sensors. In another embodiment, the height is determined by a function that relates detected light received by the at least two detectors to a position of a surface. In a further aspect, the collection module comprises three or more detectors and the function further relates detected light received by the three or more detectors to a position of a surface and a longitudinal magnification factor, M.

In an alternative embodiment the invention pertains to a method of determining height. One or more source lines or points are directed towards a specimen having a plurality of surfaces at different relative heights. Light reflected from the surfaces is detected. The reflected light is detected by at least two detectors that are positioned to receive light reflected from a one of the surfaces. A first one of the detectors receives more reflected light from a position before an focal point and a second one of the detectors receive more reflected light from a position after the focal point so that the first and second detector receive light having different intensity values unless such one of the surfaces is at an optimum focus. A height is determined based on the detected light intensities received by the at least two detectors from two of the surfaces.

In one aspect, illumination light is received and a source point of the illumination light is directed via a source pinhole onto the specimen. A first pinhole is positioned before the focal point through which a portion of the reflected light is passed to the first detector, and a second pinhole is positioned after the focal point through which a portion of the reflected light is passed to the second detector, wherein the first and second detectors are photodiode detectors. In another aspect, illumination light is received and a source line of the illumination light is directed via a source slit onto the specimen. A first slit is positioned before the focal point through which a portion of the reflected light is passed to the first detector, and a second slit is positioned after the focal point through which a portion of the reflected light is passed to the second detector, wherein the first and second detectors are photodiode arrays.

In another example, illumination light is received and a source line of the illumination light is directed via a source slit onto the specimen, wherein the first detector is positioned before the focal point and the second detector is positioned after the focal point, and wherein the first and second detectors are photodiode arrays. In yet another example, illumination light is received and a plurality of source lines or points of the illumination light is directed via a plurality of source pinholes or slits onto the specimen, and wherein the at least two detectors are two dimensional image sensors.

In one aspect, height is determined by a function that relates detected light received by the at least two detectors to a position of a surface, and the reflected light is detected by three or more detectors. In this aspect, the function further relates detected light received by the three or more detectors to a position of a surface and a longitudinal magnification factor, M.

In another disclosed embodiment, an apparatus includes an illumination module for directing a source line or point towards a specimen having a plurality of surfaces at different relative heights and a collection module for detecting light reflected from the surfaces. The collection module comprises a rapid variable focus lens, a detector, and a collection slit or pinhole for directing light reflected from a one of the surfaces onto the detector. The system also includes a processor system for determining a height between two surfaces based on the detected light received from the two surfaces at least two different focus depths.

In yet another embodiment, the system includes an illumination module for directing a plurality of source lines or points towards a specimen having a plurality of surfaces at different relative heights, and the source lines or points are directed towards the specimen at different depths of focus. The system also has a collection module for detecting light reflected from the surfaces, and the collection module contains at least two detectors that are positioned to receive light reflected from the surfaces. The at least two detectors are arranged to receive light reflected in response to the source lines or points at the different depths of focus so that each detector receives different depth of focus light. This system also has a processor system for determining a height based on the detected light received by the at least two detectors from two of the surfaces. In a further aspect, the illumination module is further configured to direct the source lines or points onto different xy positions on the specimen.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction

Some techniques for determining height may include: (1) triangulation, (2) geometric shadow, (3) use of various confocal microscopes, and (4) use of white-light (or broadband light) interferometers. The first two methods have started to fail the current precision requirements in contemporary MEOL (mid-end-of-line) or BEOL (back-end-of-line) applications. The last two methods typically fail to meet current throughput requirements.

The confocal methods are typically configured with respect to a chromatic, spinning disk, or scanning tool. The confocal method is typically slow, for both chromatic and scanning schemes. In the chromatic layout, each point on the sample corresponds to a measurement of a spectra. Multi-frames have to be taken for the scanning scheme. The scanning scheme also needs to overcome the finite fill ratio, e.g., the pin-hole to pitch ratio.

White-light interferometry can provide a high-resolution method for 3D inspection and metrology in the semiconductor industry. There are two types of such devices in the market: (1) scanning white-light interferometers ("SWI") and (2) spectroscopic white light interferometers. In SWI devices, either the sample (e.g., the wafer under inspection) or the inspection optics scan along a direction perpendicular to the wafer surface, such as the z-direction, for a distance. Multiple frames are taken at specific z-values to determine the height measurement for a specific x-y location on the wafer surface. Such SWI devices are robust, but are generally slow since they require multiple z measurements for each xy location. Furthermore, this technique requires the sample to move to a field of view and be stabilized before a measurement is taken, which limits the speed when a whole wafer is scanned, for example. Likewise, throughputs for current spectroscopic white-light interferometers are also slow for meeting the needs in the semiconductor industry.

An auto-focus mechanism can also be used for an optical probe (OP) in semiconductor inspection and metrology processes. In this technique, a chopper is used to test if the focal point is on, behind, or after the pre-set position, with uses similar principals such as the Foucault test. Light passes through the chopper to a bi-cell photodetector. The bi-cell photodetector and chopper are electronically connected with a lock-in amp. When the light is on-focus there is zero phase shift between the reference signal from the chopper and the signals from the two channels of the bi-cell photodetector. If the light is under-focus or over-focus, then the phase of a cell is shifted negative or positive, respectively, to a reference signal, and the phase of another cell is shifted in an opposite direction. With a 100× objective, this method can detect and servo-loop to control the focus better than 20 nm. However, the throughput of the chopper technique is limited.

In sum, triangulation and geometric shadow techniques typically do not provide required accuracy and precision for 3D inspection when the target structure height shrinks below 15 micron. Confocal and interferometry methods often do not provide required throughput or are too expensive for 3D inspection in, for example, in MEOL or BEOL.

Example Embodiments for Determining Structure Height

Certain embodiments of the present invention provide a new approach so as to reach high accuracy height determination concurrently with high speed. Certain embodiments of the present invention include apparatus and methods for measuring structure height on a semiconductor wafer using differential detectors to estimate the focal point shift that corresponds to the height information of the object under test without obtaining additional measurements under different illumination conditions or z positions at a same test site. To illustrate the operation clearly, two general exemplary implementations, namely point scanning and line scanning layout, are described herein. Additionally, a fast focus differential detection embodiment is also described.

The point and line scanning systems each may generally include an illumination module for directing one or more source lines or points towards a specimen having a plurality of surfaces at different relative heights. The systems also may include a collection module for detecting light reflected from two of the surfaces, and such collection module contains at least two detectors that are positioned to receive light reflected from the two surfaces. At least a first detector will tend to receive more reflected light from a position before a focal point and at least a second detector will tend to receive more reflected light from a position after the focal point so that the first and second detector receive light having different intensity values unless at an optimum focus. One or more processors may also be configured for determining a height between the two surfaces based on the light intensity sensed by the two (or more) detectors.

Figure 1A:
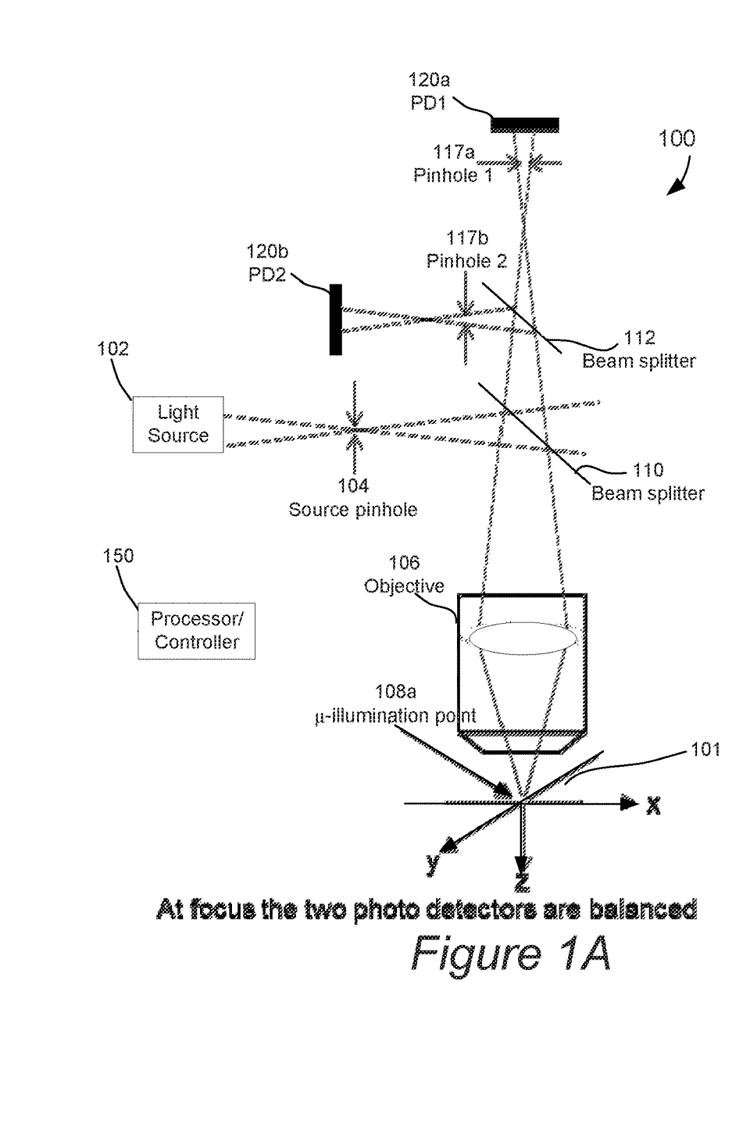
FIGS. 1A and 1B are diagrammatic representations of a point scanning system having differential detectors in accordance with one embodiment of the present invention.
Figure 1B:
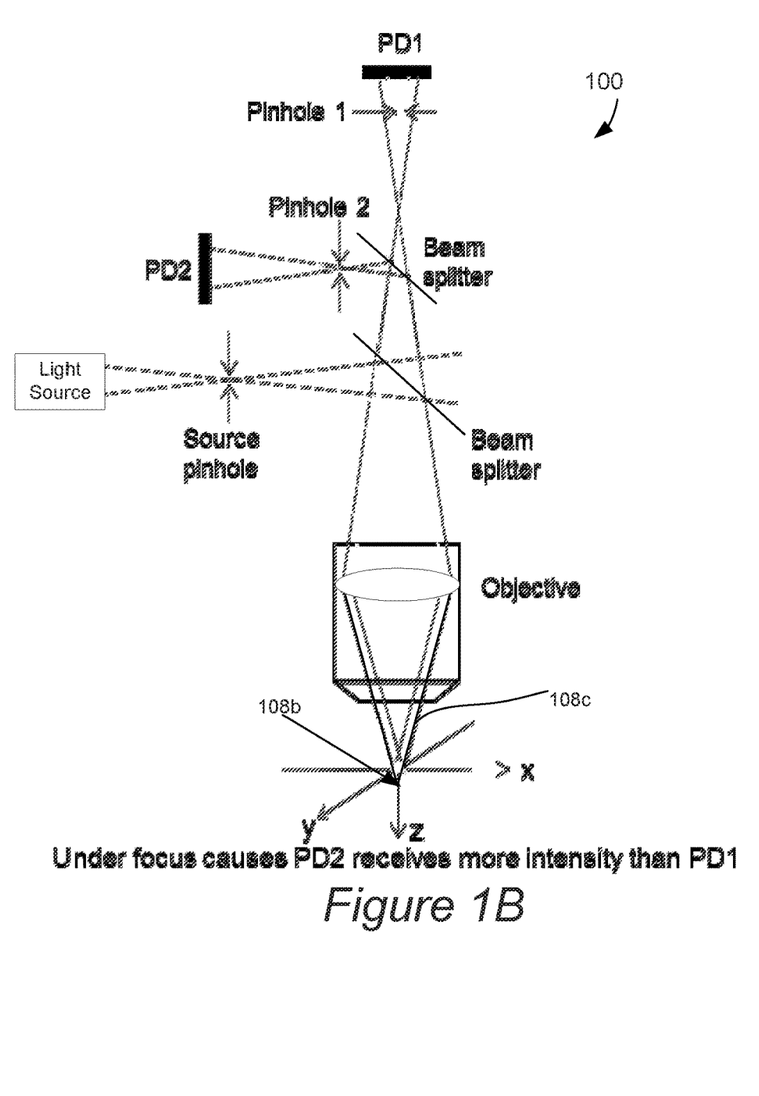

FIGS. 1A and 1B are diagrammatic representations of a point scanning system 100 having differential detectors in accordance with one embodiment of the present invention. As shown, the system 100 includes a light source 102 for generating one or more light beams. The light source may take any form for generating one or more electromagnetic waveforms. Multiple light sources may also be used. The one or more light sources may generate light having only one wavelength (e.g., monochromatic light), light having a number of discrete wavelengths (e.g., polychromatic light), light having multiple wavelengths (e.g., broadband light), and/or light that sweeps through wavelengths, either continuously or hopping between wavelengths (e.g., tunable sources or swept sources). For instance, different wavelengths may be used with different materials to achieve transparency or opaqueness with respect to the incident light on the material under test. A laser light source can be used for the light source 102, which can provide a higher brightness compared to spectroscopic methods, such as white light interferometry and chromatic confocal microscopy. Laser light sources, such as diode lasers, improve lifetime, stability, and thermal control of the light source. Other examples of suitable light sources are: a white light source, an ultraviolet (UV) laser, an arc lamp or an electrode-less lamp, colored or white light emitting diodes (LEDs), a laser sustained plasma (LSP) source, for example, those commercially available from Energetiq Technology, Inc. of Woburn, Mass., a supercontinuum source (such as a broadband laser source) such as those commercially available from NKT Photonics Inc. of Morganville, N.J., or shorter-wavelength sources such as x-ray sources, extreme UV sources, or some combination thereof. The light source(s) may also be configured to provide light having sufficient brightness, which in some cases may be a brightness greater than about 1 W/(nm cm2 Sr). The metrology system may also include a fast feedback to the light source for stabilizing its power and wavelength. Output of the light source can be delivered via free-space propagation, or in some cases delivered via optical fiber or light guide of any type.

The system 100 may also include a source pinhole 104 through which the generated light beam is directed and reflected from a first beam splitter 110 and projected through objective 106 onto a sample 101, such as a semiconductor wafer having various surfaces or structures with different relative heights. The objective 106 may be a high magnification objective lens, such as a tele-centric type. Some or all of the incident light passes through the objective lens 106 onto at least a portion of the sample 101 at point (e.g., 108a in FIG. 1A). The spot size of the incident light at the illumination point may be diffraction limited.

The wafer 101 may also be disposed on a stage (not shown) configured to position the wafer 101 to receive the incident light at particular measurement sites. The stage can be fixed or can scan in the x-direction, y-direction, and/or z-direction. The wafer 101 may be clamped to the stage in one instance, such as through mechanical and/or electrostatic clamping. For example, the stage can translate the wafer 101 in a plane perpendicular to the axis of the incident light 106 (e.g., the x-y plane) or a direction that is parallel to such incident axis (e.g., the z axis).

Light is then reflected and scattered from the wafer 101 and collected through objective 106. This system also includes a second beam splitter 112 that is positioned in the path of the reflected light and is constructed from materials so as to divide the reflected beam into two output beams. The orientation and thickness of beam splitter 112 relative to 110 is selected to manage image quality. First and second pinhole 117a and 117b are each positioned in each of the divided beam paths, respectively. The first pinhole 117a is positioned before the focal point, and the second pinhole 117b is positioned after the focal point. The system also includes two detectors 120a and 120b, e.g., photodiode detectors (PD1 and PD2), for each receiving the divided output light via their respective pinholes and outputting an output signal or image corresponding to the detected output light.

The pinhole size tends to be smaller than the actual beam size at the position of the pinhole, so a part (e.g. ~50%) of the light is blocked by the pinholes. When the structure surface being imaged is at a focal plane (e.g., 108a as shown in FIG. 1A), the light intensity received on photo detector 1 and 2 are equal or "balanced." In reference to FIG. 1B, the structure under test is not positioned at the optimum focal plane. In this example, the reflect point 108b off of the actual structure's top surface is lower than the focal point of the source pinhole 108a so that the reflected beam 108c is focused below the illumination focal point. Now the first pinhole 117a blocks more output light due to larger spot on such first pinhole 117a. In contrast, the second pinhole 117b blocks less output light since the beam is closer to focus at the first pinhole 117a. In this case, the PD2 (120b) receives a higher output intensity level than PD1 (120a).

Figure 1C:
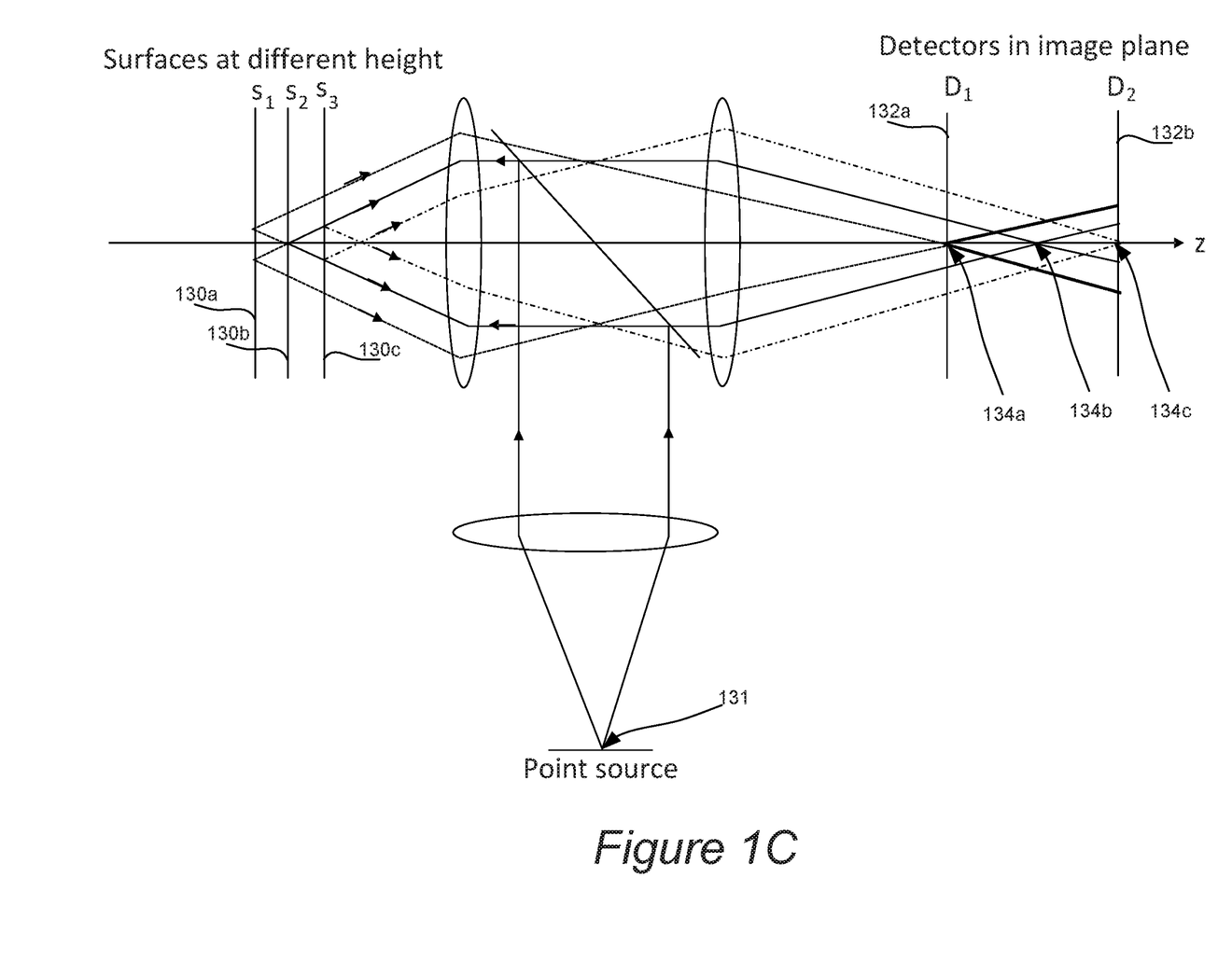
FIG. 1C is a simplified diagrammatic representation of reflection from three different surfaces in accordance with one implementation of the present invention.

FIG. 1C is a simplified diagrammatic representation of reflection from three different surfaces in accordance with one implementation of the present invention. This drawing shows three different alternative surface heights $S_1$-$S_3$. Surface $S_3$ is shown as being positioned at a greater height than $S_2$, which is positioned at a greater height than $S_1$. FIG. 1C illustrates the ray behavior for surfaces that are in focus, under-focused, and over-focused. In this example, the point source 131 is shown as being focused onto surface $S_2$ (130b). This point source 131 also shown as being under-focused with respect to surface $S_3$ (130c) and over-focused with respect to surface $S_1$ (130a).

In this example, there are two detectors $D_1$ and $D_2$ positioned in the image space such that the focal point for surface $S_2$ (134b) is at a position that is midway between the positions of $D_1$ and $D_2$. In this example, the under-focused reflected light from surface $S_3$ (134c) focuses at the position of detector $D_2$, while the over-focused reflected light from surface S (134a) focuses at the position of detector $D_1$.

In one example implementation, the collection pinholes are placed so that focal points reflected from the expected range of heights are all projected between or on the two detectors. The spacing between two detectors can be flexible, and there is a trade-off between measurement range (the farther away two detectors are, the larger z range) and measurement precision (when the surface position is too far out of focus, a detector signal become too weak and measured intensity is weak compared to noise). On average, the two detectors can be placed at the same length as the FWHM (full width at half maximum) depth of focus in the image space.

In general, the collection pinholes may also be placed relative to one another and their corresponding detectors based on the expected range of surface position values relative to expected illumination focal points. Placement of the collection pinholes also is preferably selected to result in collection of enough light for comparison between the amounts of light from both detectors without having noise levels that are higher than such collected signal levels, e.g., within signal-to-noise (SNR) requirements. For instance, the collection pinholes are placed so as to have a SNR value that is greater than about 1 or greater than about 50.

Figure 1D:
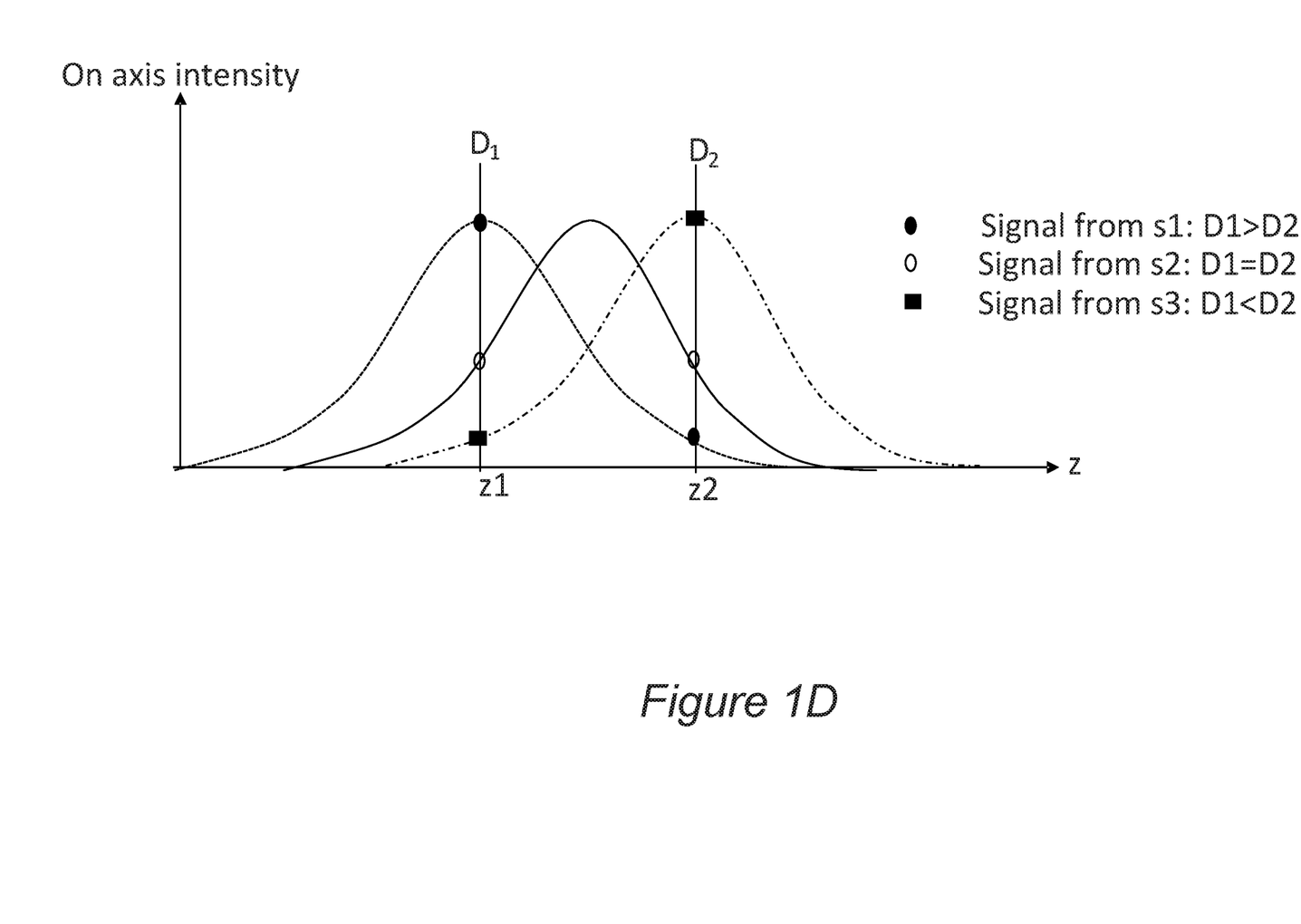
FIG. 1D is a graph of detected z axis intensity from the three surfaces of FIG. 1C as a function of z position.

FIG. 1D is a graph of detected z axis intensity from the three surfaces of FIG. 1C as a function of z position. Each curve is the on-axis z intensity distribution of the light reflected back from the different surfaces $S_1$, $S_2$, and $S_3$, which is also the output signal of a pinhole (or slit) detector located at the position of z. The two vertical lines mark the position of two detectors $D_1$ and $D_2$, and their respective outputs in responding to different surface positions reflected light.

The level of intensity depends on the amount of de-focus on the particular surface being tested and the particular position of each detector. The detectors are arranged so that they receive different amount of intensity when the light is under- or over-focused. As illustrated in FIG. 1D, the detector $D_1$ receives more light than detector $D_2$ when light is under-focused and reflected from surface $S_1$. Likewise, detector $D_2$ receives more light than detector $D_1$ when light is over-focused and reflected from surface $S_3$. In contrast, both detectors $D_1$ and $D_2$ receive substantially equal light reflected from surface $S_2$ when the source point is focused on surface $S_2$.

It is also noted that the peak for the different surfaces, occur at different z positions and are captured by different detectors. For instance, the peak for the signal from $S_1$ is captured by detector $D_1$ at position z1, while the peak for signal $S_3$ is captured by detector $D_2$ at position z2. In fact, the intensity values between the different surface curves are significantly different from each other at a wide range of z positions, except when the structure's surface matches the illumination focus point or is at optimum focus. Said in another way, the detectors can also be positioned relative to the pinhole so that one detector receives a maximum amount of light for a maximum expected under-focus value and the other detector receives a maximum amount of light for a maximum expected over-focus value.

The height difference between two different surface positions is $Ht=S_a-S_b$, and such Ht can be calculated based on the equations below. M is the longitudinal magnification factor, which is known by optics design. However, the magnification may be dependent on surface property, for example, a mirror surface M is 2× greater than a diffusive surface or a point object.

$$D = f(z) = f(M_s)$$

$$D_a = F(s_a)$$

$$D_b = F(s_b)$$

$$\frac{D_a - D_b}{D_a + D_b} = \frac{F(s_a) - F(s_b)}{F(s_a) + F(s_b)}$$

The function F is generated in order to calculate height. Function F can be known for well-corrected optics. Alternatively or additionally, function F can be calibrated using known sample surfaces. The simplest case is to assume that F is a Gaussian function by taking the normalized differential signal, which allows some common intensity factors in F to be cancelled. Because M changes with surface types, more than two detectors may be used so that M can also be calculated from the signals of the multiple detectors.

The function F can then be used to convert the intensities from PD1 and PD2 to the height between two surfaces of the reflection point from such two different surfaces. Any suitable function F may be generated for converting the detected differential signals from multiple positioned detectors and multiple surfaces into a height metric. For instance, an example function F of confocal z response may be expressed as:

$$F(z) = \left[\frac{\sin(u/4)}{u/4}\right]^2$$

$$u = \frac{2\pi}{\lambda}(NA)^2 z$$

Where NA is the numerical aperture of the objective, and $\lambda$ is the wavelength.

Alternatively, the function can be approximated by a Gaussian function within a small range of defocus:

$$D_1 = I_0 e^{-2\frac{(z_0-z_1)^2}{w^2}}$$

$$D_2 = I_0 e^{-2\frac{(z_0-z_2)^2}{w^2}}$$

$$\frac{D_1}{D_2} = e^{-4\frac{z_0 \Delta}{w^2}}$$

Where w is the 1/e2 width of depth of focus, $I_0$ is a scaling factor, $\Delta = z_1 - z_2$ is the distance between the two detectors, and $z_0$ is the peak position of the focus response curve of a surface to be measured, which can be derived from the ratio of two detector signals:

$$z_0 = \frac{w^2}{4\Delta}\ln\left(\frac{D_1}{D_2}\right)$$

The z height of a surface is then given by:

$$s = \frac{w^2}{4\Delta M}\ln\left(\frac{D_1}{D_2}\right)$$

$$= k\,\ln\left(\frac{D_1}{D_2}\right)$$

where $D_1$ is the intensity value from the first detector, $D_2$ is the intensity value from the second detector, M is the longitudinal magnification of the optics, and k is a scaling factor. Scaling factors, such as $I_0$ and k, can be determined from experimental measurements on known surface positions (or z positions), and known focus positions (optimum, under- and over-focus). When M is unknown or is affected by sample properties, k becomes dependent on sample properties, which are unknown. More than 2 detectors may then be used to measure z height so that k can be cancelled by comparing the ratio of more than one pair of detectors. The above function F may also be calibrated for different operating conditions, such as different wavelength ranges that may be used in a height determination process as described herein.

A function or model for determining height based on measured difference or ratio signals may be generated by any suitable technique. For instance, a plurality of known heights may be obtained by measuring the heights of a calibration wafer having a plurality of structures at varying heights. Difference or ratio detected signals can then be obtained from the known structures and used to generate the model. For instance, the model may take the form of the above described equations for determining height. The constant k can be determined based on the calibration wafer. In an alternative example, a plurality of known heights and difference or ratio signals may be simulated and used to generate the height model. In yet another embodiment, a reference method may be used to generate the function between the detected different or ratio signals to structure height for a specific type of application, during the recipe setup.

Figure 2A:
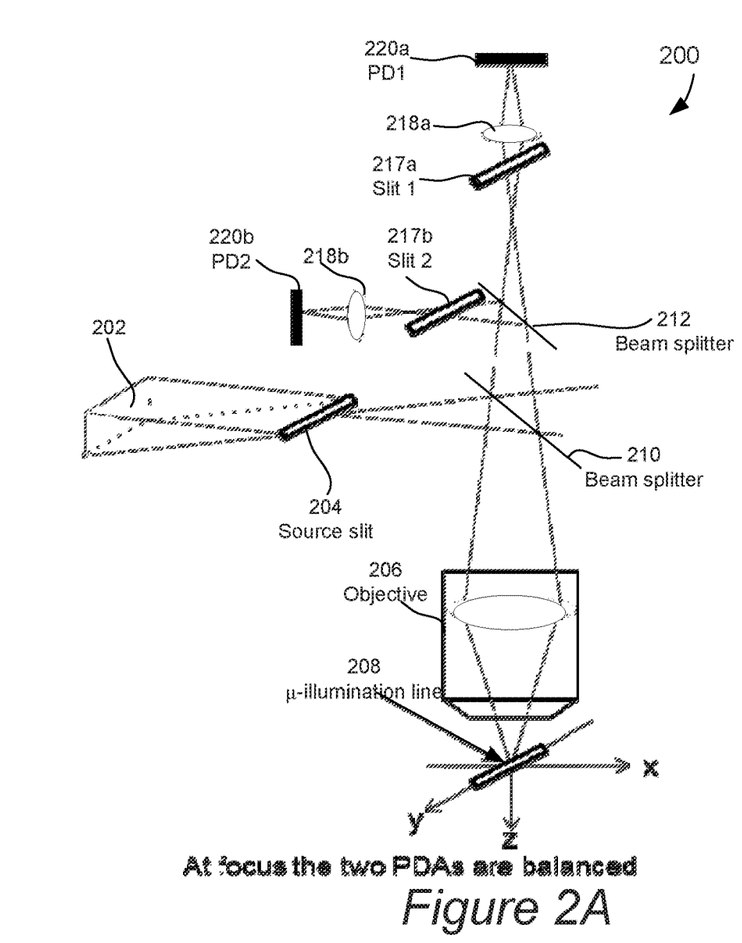
FIGS. 2A and 2B are diagrammatic representations of a line scanning system having differential detectors in accordance with two alternative embodiments of the present invention.
Figure 2B:
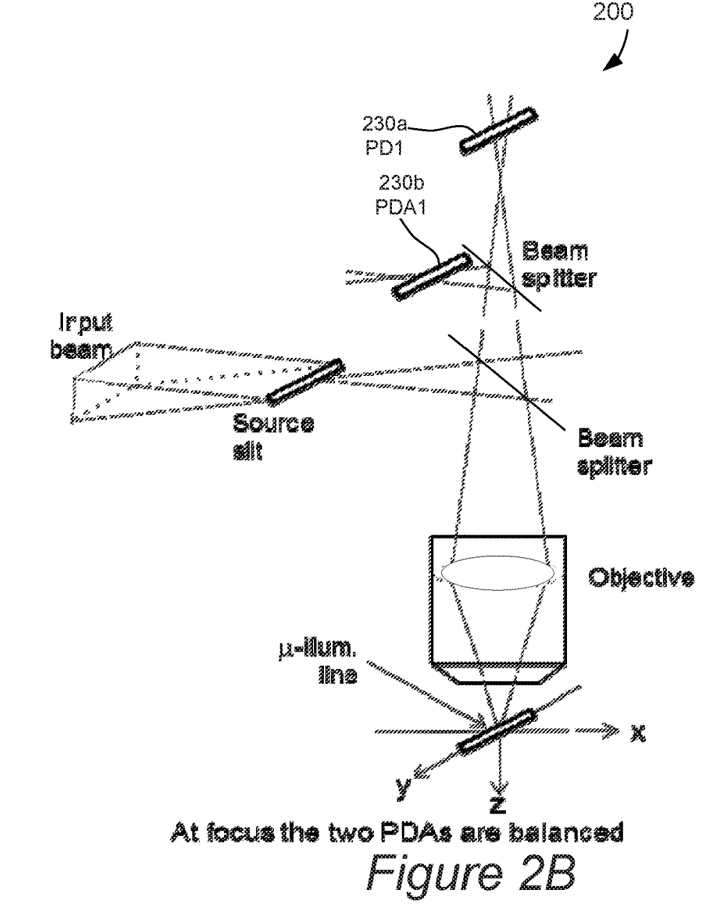

The differential detection principles described above for a pinhole system (e.g., as illustrated with FIGS. 1A-1D) can be extended into a line scanning scheme. FIGS. 2A and 2B show exemplary embodiments of such extension. As shown in FIG. 2A, a line of incident light 208 is illuminated onto the wafer by passing the incident light 202 through a source slit 204. Scanning a line of incident light across the sample, of course, results in a faster technique. This alternative system 200 may also include two slits 217a and 217b that replace the two pinholes 117a and 117b of the system 100 of FIGS. 1A and 1B. This line scan system 200 may also include two photo-detector-arrays (PDA) 220a and 220b that replace the two PDs 120a and 120b, respectively, of the system 100 of FIGS. 1A and 1B.

Although not required, system 200 may also include any suitable lenses, such as 218a and 218b, for further focusing the output light onto each corresponding PDA so as to achieve a higher light efficiency level and provide adequate lateral resolution along the line. That is, the line scheme system 200 may also include two lenses 218a and 218b that are added before the two PDAs so as to better resolve the spatial resolution along the line of each slit, resulting in each point on the wafer being sharply imaged along the line onto the PDAs at least when the wafer is on focus. The PDAs may also be positioned so that the off focus points on the wafer are within or nearly in the depth of focus of the system.

FIG. 2B illustrates a simplified version of a line scan scheme in accordance with another embodiment of the present invention. For the simplified version, the slit function is replaced by the finite width of PDAs 230a and 230b. Thus, the two lenses before the PDAs (lens 218a and 218b as shown in FIG. 2A) can be eliminated.

The above-described method for converting detected signals into a height value may be extended to a line scanning system. For example, the detected intensity values from pixels of PDA1 and PDA2 corresponding to the same point on wafer may be processed in the same way described above, in a point-by-point style along the line.

Figure 3A:
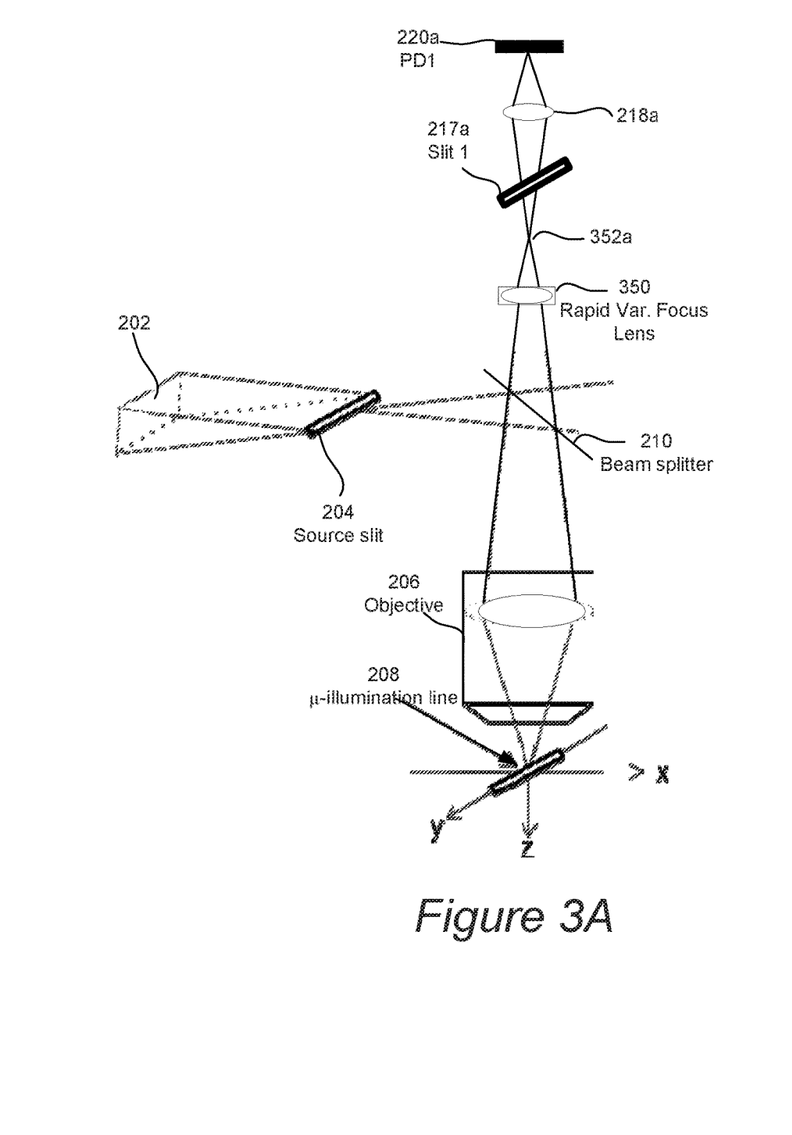
FIGS. 3A and 3B illustrate a line scheme system having a rapid variable focusing lens in accordance with another implementation of the present invention.
Figure 3B:
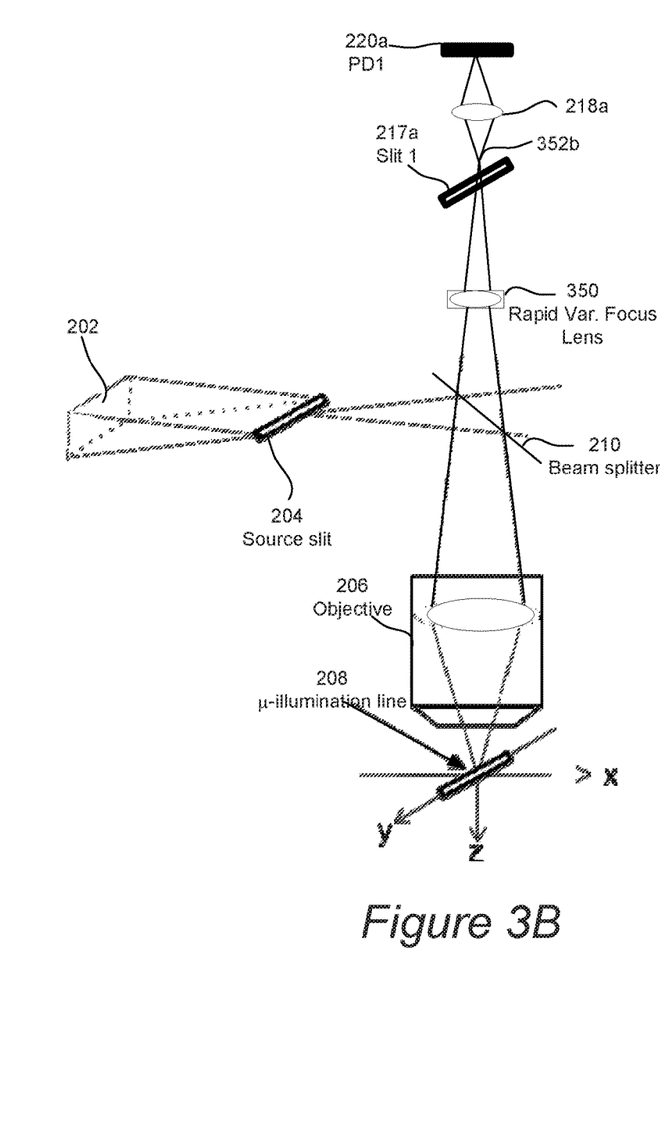

Another alternative system may implement a rapid variable focusing lens (such as Liquid Lens by VariOptic, a business unit of Parrot of Paris, France) to replace the second beam splitter 212, second slit 217b, and second PDA 220b of FIG. 2A or 2B. FIGS. 3A and 3B illustrate a line scheme system having a rapid variable focusing lens (or liquid lens) 350 in accordance with another implementation of the present invention. In this alternative, the liquid lens 350 is set at first focal length to focus the source slit before slit 217a at point 352a as shown in FIG. 3A. A measurement is taken at this first focal length. The liquid lens 350 is then set at second focal length to focus the source slit after slit

217a at point 352b as shown in FIG. 3B. Another measurement is then obtained. A similar algorithm may then be used to convert these two measurements from two surfaces into height.

Figure 4A:
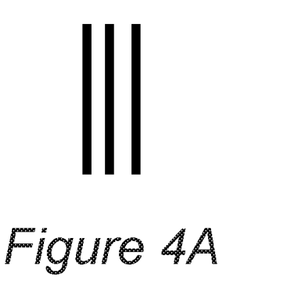
FIG. 4A illustrates a system using parallel source slits in accordance with an alternative embodiment.
Figure 4B:
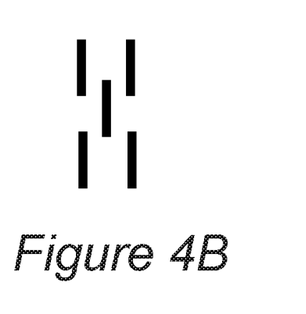
FIG. 4B illustrates a system using a checkboard pattern of source slits in accordance with another alternative embodiment.

The line scheme embodiments can also be altered further into an area detection scheme. For example, the source slit can be extended as strip lines (FIG. 4A) or a checkerboard pattern (FIG. 4B), and the PDAs replaced by 2-dimensional pixelated image sensors, such as CCD, CMOS, or the like. The multiple strip lines or checkerboard pattern of lines can be achieved by any suitable beam splitting mechanism, such as diffractive optical elements (DOE's), prisms, etc. In certain embodiments, the pixels of each detector are aligned with the pixel structure of the corresponding illumination structure. In these area schemes, more data can be obtained from the 2-dimensional detectors, which may also allow determination of how much the system is out of focus and a higher signal to noise ratio.

In any of the embodiments described herein, any suitable number of detectors can be used. When more than two detectors are used, preferably the detectors are positioned at about equal distance along z axis. For instance, more than two PD's or PDA's may be used to obtained a greater amount of data, as compared with using only two PD's or PDA's. The different detectors can be placed at different positions relative to the expected focus or height range. Increasing the number of detectors tends to resolve the ambiguity in determining surface height when surface properties changes are unknown. More detectors also result in an increased signal to noise ratio or extended measurement height range of the structures on wafer.

When more than two detectors are used, a function may be generated based on known heights or a well-known/simulated optics system and the relative positions of the detectors with respect to a plurality of known measurements at a set of known z positions. The focus function F may not need to be known as long as there are enough number of detectors to determine the function F. The technique for determining height may also include using detected signals from more than two detectors in such function to determine height between two surfaces, as well as other parameters such as M, $I_0$, and k as described herein.

Figure 5A:
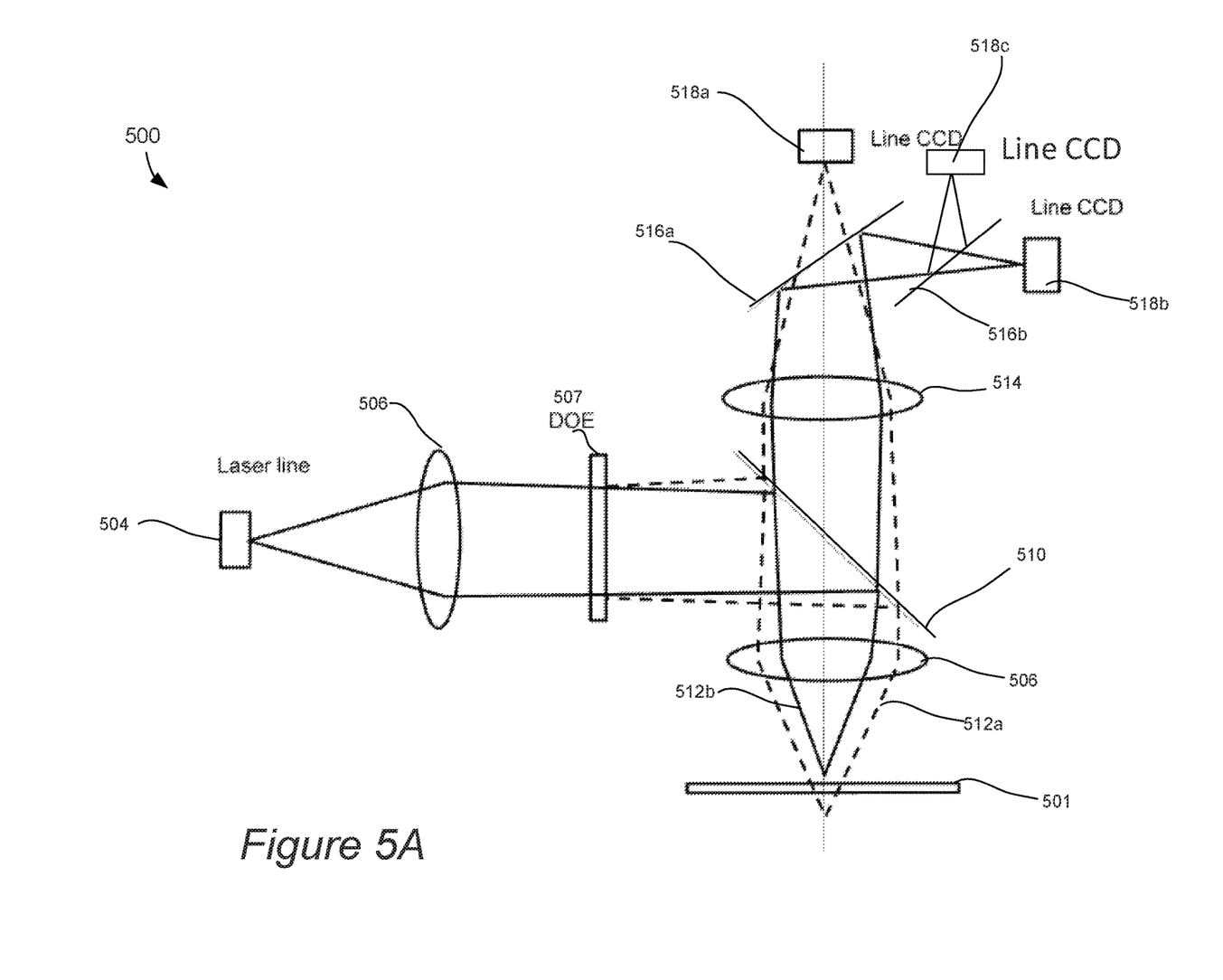
FIG. 5A is a diagrammatic view of a system for projecting multiple line scans at different focus depths in accordance with another embodiment of the present invention.

The dynamic range of measurement, which can be defined as the z range to precision ratio, can be limited for higher NA systems where DOF (depth of focus) is limited. To extend dynamic range, multiple illumination beams focused at different z height can be used. The focus of the multiple illumination beams can be spaced at about the same length of DOF at objective space. Multiple detectors can be arranged with each one positioned between the focus of adjacent beams. FIG. 5A is a diagrammatic view of a system 500 for projecting multiple line scans at different focus depths in accordance with another embodiment of the present invention. As shown, the system includes one or more lenses 506 for receiving and shaping an illumination line 504, which is directed towards an optical element (such as diffractive optical element or DOE 507) for producing multiple illumination lines. In the illustrated embodiment, two illumination beams 512a and 512b are produced by the DOE 507 and incident on the sample 501 at two different focus depths via beam splitter 510 and objective 506. Of course, more than two illumination beams, for example, in the form of two or more lines or points can be generated and directed onto the sample.

Figure 5B:
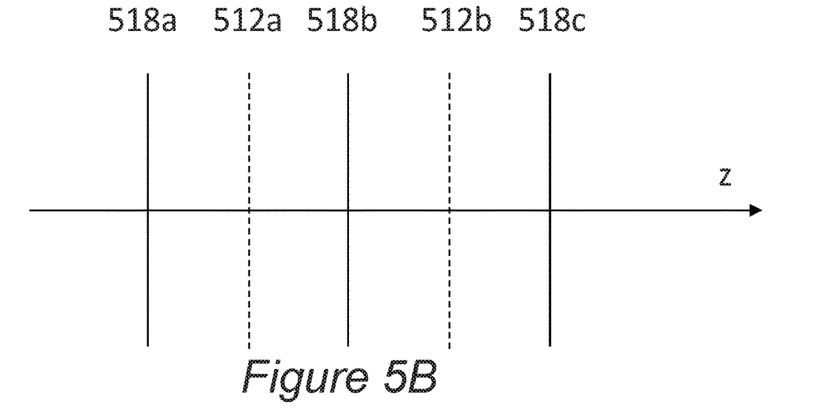
FIG. 5B illustrates relative positioning of the detectors of FIG. 5A.

Multiple output beams are then reflected from the sample in response to the multiple incident beams at the different focus depths. The multiple output beams are then focused by one or more lens (such as 514) onto two or more beam splitters (e.g., 516a and 516b), which direct the different output beams towards different detectors, such as line CCD's 518a, 518b, and 518c, respectively. The CCDs are positioned such that the two reflected focus points of the two beams (512a and 512b) are located in between the z position in image space of two adjacent CCDs (see FIG. 5B). Therefore, the dynamic range is extended by 2× compared to a single beam configuration. For example, detector pairs of 518b and 518c can still generate measurements when the surface height is out of the range of CCD pair 518a and 518b.

In addition to offsetting multiple illumination lines or points within the z direction, these multiple incident lines and points can also be offset in the xy direction plane. In this later embodiment, the beam splitter can be replaced by a simple mirror or prism that reflects the offset output beams to different offset detectors, which allows for detection of a higher percentage of each output beam, as compared to a beam splitter, which loses 50% of the beam by way of example. Any of the above described embodiments may implement such simple mirror or prism.

The above described embodiments use at least two intensity values for each pair of surfaces to determine the height between such surfaces. These apparatus and technique are more efficient than the chromatic confocal scheme that uses a spectra range, when intensity is fanned out with wavelengths and each pixel detects the intensity within the corresponded and limited wavelength bandwidth. Also, the number of digitized operations per point on wafer for certain embodiments may be significantly less than a chromatic scheme in which hundreds of digitized numbers are required to get the spectra information. Thus, certain apparatus and technique embodiments of the present invention tend to be significantly faster. Additionally, confocal systems that use a pinhole array at the illumination leaves gaps between pinholes and requires methods to cover those holes, which also reduces operation efficiency.

The two or more output signals or light beams acquired from the measurement sites may be detected as any signal type that can be subtracted from each other or otherwise compared with one another, by adding additional light state control elements in the beam path, such as polarization control elements, wavelength control elements, and beam propagation direction control elements. Example signals include, but are not limited to, any type of scatterometry, spectroscopic, ellipsometry, and/or reflectometry signals, including: Ψ, Δ, Rs (complex reflectivity of the s polarization), Rp (complex reflectivity of the p polarization), Rs ($|r_s|^2$), Rp ($|r_p|^2$), R (unpolarized reflectivity), α (spectroscopic "alpha" signal), β (spectroscopic "beta" signal), and functions of these parameters, such as tan(Ψ), cos(Δ), ((Rs−Rp)/(Rs+Rp)), Mueller matrix elements ($M_{ij}$), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. Other embodiments may use monochromatic or laser light sources where at least one of the signals may be obtained at a single wavelength, instead of multiple wavelengths. The illumination wavelengths could be any range, e.g., from X-ray wavelengths to far infra-red wavelengths.

Figure 6:
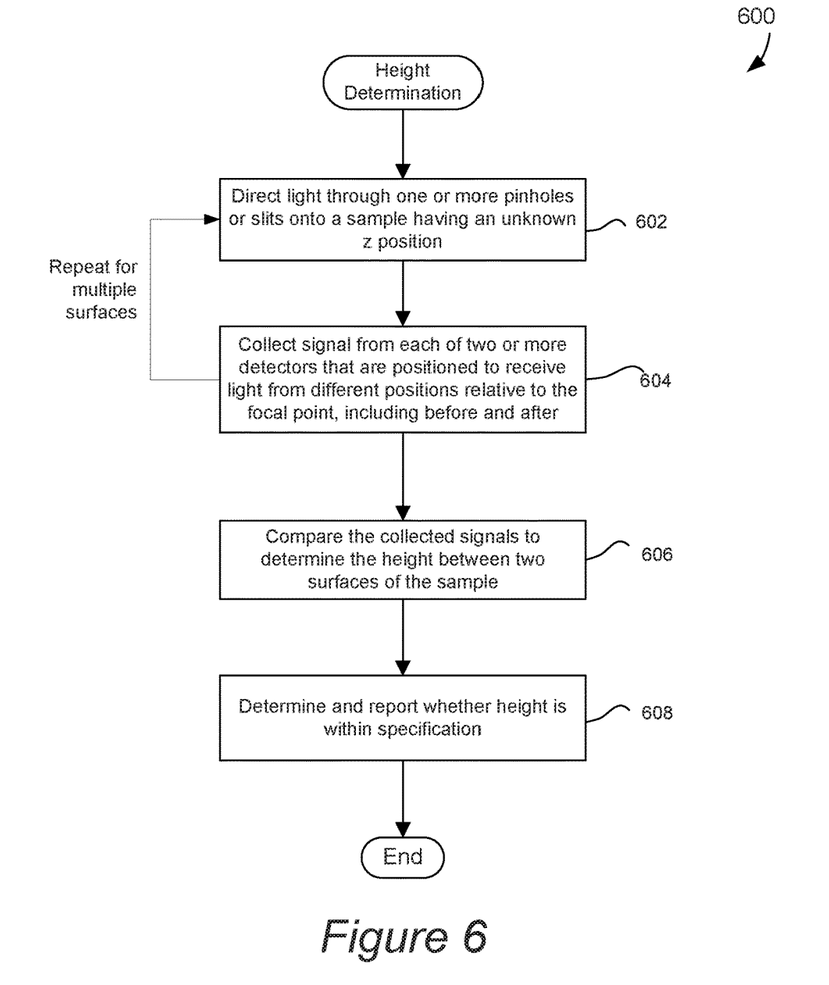
FIG. 6 is a flow chart illustrating a procedure for determining height of a structure in accordance with one embodiment of the present invention.

FIG. 6 is a flow chart illustrating a procedure 600 for determining height of a structure in accordance with one embodiment of the present invention. Light is directed through one or more pinholes or slits onto a sample having a surface with an unknown z position in operation 602. A signal may then be collected from each of two or more detectors that are positioned to receive light from different positions relative to the focal point in operation 604. For instance, the different positions correspond to having a collection pinhole/slit before the focal point and a collection pinhole/slit after the focal point.

The measurements may include any suitable radiation signals, such as scatterometry, reflectometry, or ellipsometry signals, including examples described herein. The type of acquired signals may be selected based on signal sensitivity to the structure of interest. For instance, certain wavelengths and certain polarization states may be more sensitive to certain particular structure dimensions or with different surface roughness or deposited layers. The structures of interest may include any 3D structures, such as TSV's, bumps, multilayer structures/stacks, etc.

Operations 602 and 604 are repeated for at least another surface so as to obtain pairs of surfaces between which a relative height is to be determined. For instance, one surface may be in the form of a substrate, while the other surface is the top of a TSV structure. After the signals for two or more surfaces are acquired, the collected signals may then be compared to determine the height difference between two surfaces of the sample in operation 606. If there are only two signals collected for each particular surface of interest, then the signals can be simply subtracted to obtain a difference signal or divided to obtain a signal ratio, which results can then be input into a function that relates such differential signals to height. If there are more than two signals collected for each surface by three or more detectors, any number of techniques may be used. For instance, a function may be generated to relate three or more signals to height. In another simpler use case, the addition measurement can be used as a redundant measurement to suppress noise or improve measurement accuracy.

Alternative algorithms for processing the detected signals may include combining the three or more signals to obtain a single difference signal, such as a difference or ratio signal. For instance, the highest signal difference or ratio, which corresponds to a pair of signals, may then be optionally selected and analyzed to determine height. In another example, the difference/ratio signals may be reduced to a single difference/ratio value, such as an average difference or ratio value. That is, the average of the difference/ratio signals for the different detector pairs may be determined to obtain an average difference/ratio signal, in such that way that noise can be reduced from the extra measured signal with minimum penalty to signal process.

Once the height is determined, it may be determined and reported whether such height is within specification in operation 608. The height specification may be defined based on any suitable height thresholds or percentage values, for example, as compared to average differences. For instance, height values that are inside a predefined range may result in a quality indication of "good"; otherwise, height values that are outside the predefined range may reported as a "poor" quality indication. The procedure may then end or be repeated for multiple targets.

Certain model-less embodiments of the present invention may be extended by training techniques for known quality structures (e.g., known poor and good height ranges and corresponding intensity values for different focus values). An algorithm based on machine-learning methodology, such as neural networks, may be used to relate measured signals to pre-programmed variations in a test structure, such as a TSV structure, or Cu-pillar height, based on a training set of known structures. That is, a training set with predefined or known variations can be measured to obtain signals to determine a model for relating detected signals to feature or process variations. After the machine learning operation is completed, feature and process-related parameters can be extracted from signals obtained from structures of interest having unknown characteristics using such model.

In further embodiments, certain process parameters are varied. For instance, electric plating conditions for a Cu-pillar structures or etching conditions related to produce the TSV structures may be used as another way to create a DOE (design of experiment) training set, e.g., different wafers are processed at different plating or etching conditions.

After a DOE training set is created, targets that were fabricated using different process conditions can be measured to obtain signals, such as particular signal type from a single measurement site at two or more different focal positions from multiple measurement sites, which are then processed as a part of the training algorithms. To determine height parameters for the training set, these targets from the training set may be characterized by a reference metrology that can be destructive, e.g. cross-section TEM or non-destructive, e.g. by atomic force microscopy (AFM) or CD-SEM. The known feature parameters may simply include indications as to poor or good quality, rather than specific metrology values.

Any suitable combination of hardware and/or software may be used to implement any of the above described techniques. In a general example, a metrology tool may comprise an illumination module which illuminates a target, a collection module which captures relevant information provided by the illumination system's interaction (or lack thereof) with a target, device or feature, and a processing system which analyzes the information collected using one or more algorithms. Metrology tools can generally be used to measure various radiation signals pertaining to structural and material characteristics (e.g., material composition, dimensional characteristics of structures and films such as film thickness and/or critical dimensions of structures, overlay, etc.) associated with various semiconductor fabrication processes. These measurements can be used to facilitate process controls and/or yield efficiencies in the manufacture of semiconductor dies.

The metrology tool can comprise one or more hardware configurations which may be used in conjunction with certain embodiments of this invention as described above. Examples of such hardware configurations include, but are not limited to, the following: beam profile reflectometer (angle-resolved reflectometer), broadband reflective spectrometer (spectroscopic reflectometer), single-wavelength reflectometer, angle-resolved reflectometer, imaging system, and scatterometer (e.g. speckle analyzer)

The hardware configurations can be separated into discrete operational systems. On the other hand, one or more hardware configurations can be combined into a single tool. One example of such a combination of multiple hardware configurations into a single tool is further illustrated and described U.S. Pat. No. 7,933,026, which patent is herein incorporated by reference in its entirety for all purposes. The system may include certain lenses, collimators, mirrors, quarter-wave plates, polarizers, detectors, cameras, apertures, and/or light sources. The wavelengths for the optical systems can vary from about 120 nm to 3 microns. The signals collected can be polarization-resolved or unpolarized.

The system may include multiple metrology heads integrated on the same tool. However, in many cases, multiple metrology tools are used for measurements on a single area or multiple areas on the sample. Several embodiments of multiple tool metrology are further described, e.g., in U.S. Pat. No. 7,478,019 by Zangooie et al, entitled "Multiple tool and structure analysis", which patent is incorporated herein by reference in its entirety for all purposes.

The illumination system of certain hardware configurations may include one or more light sources. In turn, one or more detectors or spectrometers are configured to receive via a collection optical elements illumination reflected or otherwise scattered from the surface of the specimen. Suitable sensors include charged coupled devices (CCD), CCD arrays, time delay integration (TDI) sensors, TDI sensor arrays, photomultiplier tubes (PMT), and other sensors. Measured spectra or detected signal data (as a function of position, wavelength, polarization, azimuth angle, etc.) may be passed from each detector to a processor system (e.g., 150 of FIG. 1A) for analysis.

It should be recognized that the various steps described throughout the present disclosure may be carried out by a single processor system or, alternatively, a multiple processor system. Moreover, different subsystems of the system, such as the above described light source and/or detector system embodiments, may include a computer system suitable for controlling system status, preprocessing signals, or carrying out at least a portion of the steps described herein. Therefore, the aforementioned description should not be interpreted as a limitation on the present invention but merely an illustration. Further, the one or more processor system may be configured to perform any other step(s) of any of the method embodiments described herein.

In addition, the processor system may be communicatively coupled to a detector system in any manner known in the art. For example, the one or more processor system may be coupled to computing systems associated with the detector system. In another example, the detector system may be controlled directly by a single computer system coupled to processor system.

The processor system may be configured to receive and/or acquire data or information (e.g., measurement signals, difference signals, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the processor system and other systems (e.g., external memory, reference measurement source, or other external systems). For example, processor system may be configured to receive measurement data from a storage medium (e.g., internal or external memory) via a data link. For instance, results obtained using the detection system may be stored in a permanent or semi-permanent memory device (e.g., internal or external memory). In this regard, the spectral results may be imported from on-board memory or from an external memory system. Moreover, the processor system may send data to other systems via a transmission medium. For instance, qualitative and/or quantitative results determined by processor system may be communicated and stored in an external memory. In this regard, measurement results may be exported to another system.

The processor system may include, but is not limited to, GPU board, FPGA, programmable logic arrays, a personal computer system, mainframe computer system, workstation, image computer, or any other device known in the art. In general, the term "processor system" may be broadly defined to encompass any device having one or more processors, which execute instructions from a memory medium. Program instructions implementing methods such as those described herein may be transmitted over a transmission medium such as a wire, cable, or wireless transmission link. Program instructions may be stored in a computer readable medium (e.g., memory). Exemplary computer-readable media include read-only memory, flash memory, a random access memory, or a magnetic or optical disk.

The metrology tool may be designed to make many different types of measurements related to semiconductor manufacturing. Certain embodiments of the invention for determining quality and/or quantitative height values may utilize such measurements. Additional metrology techniques for determining specific target characteristics may also be combined with the above-described height determination techniques. For example, in certain embodiments the tool may also measure signals and determine other characteristics of one or more targets, such as quality and defect quantity values, critical dimensions, overlay, film thicknesses, process-related parameters (e.g., plating conditions), etc. The targets can include certain regions of interest such as for example Cu-pillars for interconnections between chips. Targets can include multiple layers (or films), such as photoresist or passivation layers.

Collected data can be analyzed by a number of data fitting and optimization techniques an technologies including machine-learning algorithms such as neural networks, support-vector machines (SVM); dimensionality-reduction algorithms such as, e.g., PCA (principal component analysis), ICA (independent component analysis), LLE (local-linear embedding); Kalman filter; algorithms to promote matching from same or different tool types, and others.

Computational algorithms are usually optimized for data process speed and accuracy with one or more approaches being used such as design and implementation of computational hardware, parallelization, etc. Different implementations of algorithms can be done in firmware, software, FPGA, programmable logic array, etc.

The data analysis may be used to pursue one of the following goals: measurement of height, quality, defect number, CD, composition, films, generating process parameters (e.g., plating or etching settings), and/or any combination thereof.

Certain embodiments of the present invention presented here generally address the field of semiconductor process and quality control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:
1. A system for determining height of a semiconductor structure, comprising:

an illumination module for directing one or more source lines or points towards a specimen having a plurality of surfaces at different relative heights;

a collection module for detecting light reflected from the surfaces, wherein the collection module contains at least two detectors that are positioned to receive light reflected from a one of the surfaces, wherein a first one of the detectors receives more reflected light from a position before a focal point and a second one of the detectors receives more reflected light from a position after the focal point so that the first and second detector receive light having different intensity values unless such one of the surfaces is at an optimum focus for which such first and second detector receive light having a same intensity; and a processor system for determining a height value based on converting the detected light, which is received by each of the at least two detectors from two of the surfaces at different relative heights, into the height value for one of the two surfaces relative to the other of the two surfaces, wherein the height value is determined via a function or model based on a difference or ratio of light detected by the first and second detectors from the two surfaces.

2. The system of claim 1, wherein:
the illumination module comprises a pinhole for receiving illumination light and directing a source point of the illumination light onto the specimen; and
the collection module further comprises:
a first pinhole positioned before the focal point through which a portion of the reflected light is passed to the first detector; and
a second pinhole positioned after the focal point through which a portion of the reflected light is passed to the second detector, wherein the first and second detectors are photodiode detectors.

3. The system of claim 1, wherein:
the illumination module comprises a slit for receiving illumination light and directing a source line of the illumination light onto the specimen; and
the collection module further comprises:
a first slit positioned before the focal point through which a portion of the reflected light is passed to the first detector; and
a second slit positioned after the focal point through which a portion of the reflected light is passed to the second detector, wherein the first and second detectors are photodiode arrays.

4. The system of claim 1, wherein the collection module further comprises a pair of pinholes or slits that are positioned such that the focal point reflected from an expected range of heights for the surfaces at different relative heights is received between or on one of such pinholes or slits with respect to image space.

5. The system of claim 4, wherein the pair of pinholes or slits are positioned so as to receive different amounts of light when one of the surfaces is de-focused and equal amounts of light when such surface is in focus.

6. The system of claim 5, wherein the pair of pinholes or slits are positioned so that only one of the first and second detectors receive a maximum intensity from a particular one of the surfaces when it is de-focused by a particular amount.

7. The system of claim 1, wherein:
the illumination module comprises a slit for receiving illumination light and directing a source line of the illumination onto the specimen,
wherein the first detector is positioned before the focal point, and
wherein the second detector is positioned after the focal point.

8. The system of claim 1, wherein:
the illumination module comprises a plurality of slits or pinholes for receiving illumination light and directing a plurality of source lines or points of the illumination onto the specimen, and
the at least two detectors are two dimensional image sensors.

9. The system of claim 1, wherein the collection module comprises three or more detectors and the function or model further relates detected light received by the three or more detectors to a position of a surface and a longitudinal magnification factor, M.

10. The system of claim 1, wherein the collection module further comprises a pair of pinholes or slits that are positioned relative to the first and second detectors so that the first detector receives a maximum amount of light for a maximum expected under-focus value and the second detector receives a maximum amount of light for a maximum expected over-focus value.

11. A method of determining height, comprising:
directing one or more source lines or points towards a specimen having a plurality of surfaces at different relative heights;
detecting light reflected from the surfaces, wherein the reflected light is detected by at least two detectors that are positioned to receive light reflected from a one of the surfaces, wherein a first one of the detectors receives more reflected light from a position before an optimum focal point and a second one of the detectors receives more reflected light from a position after the optimum focal point so that the first and second detector receive light having different intensity values unless such one of the surfaces is at an optimum focus for which such first and second detector receive light having a same intensity; and
determining a height value based on converting the detected light, which is received by each of the at least two detectors from two of the surfaces at different relative heights, into the height value for one of the two surfaces relative to the other of the two surfaces, wherein the height value is determined via a function or model based on a difference or ratio of light detected by the first and second detectors from the two surfaces.

12. The method of claim 11, further comprising receiving illumination light and directing a source point of the illumination light via a source pinhole onto the specimen, wherein a first pinhole is positioned before the optimum focal point through which a portion of the reflected light is passed to the first detector and a second pinhole is positioned after the optimum focal point through which a portion of the reflected light is passed to the second detector, wherein the first and second detectors are photodiode detectors.

13. The method of claim 11, further comprising receiving illumination light and directing a source line of the illumination light via a source slit onto the specimen, wherein a first slit is positioned before the optimum focal point through which a portion of the reflected light is passed to the first detector and a second slit is positioned after the optimum focal point through which a portion of the reflected light is passed to the second detector, wherein the first and second detectors are photodiode arrays.

14. The method of claim 11, further comprising receiving illumination light and directing a source line of the illumination light via a source slit onto the specimen, wherein the first detector is positioned before the optimum focal point and the second detector is positioned after the optimum focal point, and wherein the first and second detectors are photodiode arrays.

15. The method of claim 11, further comprising receiving illumination light and directing a plurality of source lines or points of the illumination light via a plurality of source pinholes or slits onto the specimen and receiving the reflected light from the surfaces at a pair of pinholes or slits that are positioned such that the focal point reflected from an expected range of heights for the surfaces at different relative heights is received between or on one of such pinholes or slits with respect to image space, and wherein the at least two detectors are two dimensional image sensors.

16. The method of claim 11, wherein the reflected light is detected by three or more detectors, and the function or model further relates detected light received by the three or more detectors to a position of a surface and a longitudinal magnification factor, M.

17. The method of claim 11, further comprising receiving and directing a source point or slit of the illumination light via a source pinhole or slit onto the specimen, wherein a pair of pinholes or slits are positioned relative to the first and second detectors so that the first detector receives a maximum amount of light for a maximum expected under-focus value and the second detector receives a maximum amount of light for a maximum expected over-focus value.

* * * * *